United States Patent [19]
Michaelsen et al.

[11] Patent Number: 5,348,876
[45] Date of Patent: Sep. 20, 1994

[54] IGG3 ANTIBODIES WITH SHORTENED HINGE REGION AND A COMPLEMENT ACTIVATION TEST

[75] Inventors: Terje Michaelsen, Hagan; Inger Sandlie, Oslo, both of Norway

[73] Assignee: Dynal AS, Oslo, Norway

[21] Appl. No.: 838,264

[22] PCT Filed: Jul. 17, 1990

[86] PCT No.: PCT/EP90/01172
§ 371 Date: Mar. 12, 1992
§ 102(e) Date: Mar. 12, 1992

[87] PCT Pub. No.: WO91/01335
PCT Pub. Date: Feb. 7, 1991

[30] Foreign Application Priority Data

Jul. 18, 1989 [GB] United Kingdom ............... 8916400.8

[51] Int. Cl.$^5$ ...................... C12N 5/10; C12N 15/13; C12P 21/08; C07K 15/28
[52] U.S. Cl. ............... 435/240.2; 435/320.1; 530/387.3; 536/23.53
[58] Field of Search ............... 530/387.3; 435/69.6, 435/69.7, 172.3, 240.2, 320.1; 536/23.53

[56] References Cited
FOREIGN PATENT DOCUMENTS

| | | |
|---|---|---|
| 0327378A1 | 8/1989 | European Pat. Off. . |
| WO88/06837 | 9/1988 | World Int. Prop. O. . |
| WO88/07089 | 9/1988 | World Int. Prop. O. . |
| WO89/01974 | 3/1989 | World Int. Prop. O. . |

OTHER PUBLICATIONS

Bindon et al., "Human Monoclonal IgG Isotypes Differ in Complement Activating Function at the Level Of C4 as Well as C1q".

Gregory et al., "The Solution Conformations of the Subclasses of Human IgG Deduced From Sedimentation and Small Angle X-Ray Scattering Studies", pp. 821–829, 1987.

Schneider et al., "Genetically Engineered Immunoglobulins Reveal Structural Features Controlling Segmental Flexibility", pp. 2509–2513, 1988.

Sandlie et al., "C1q Binding to Chimeric Monoclonal IgG3 Antibodies Consisting of Mouse Variable Regions and Human Constant Regions with Shortened Hinge Containing 15 to 47 Amino Acids", pp. 1599–1603, 1989.

Garred et al., "The IgG Subclass Pattern of Complement Activation Depends on Epitope Density and Antibody and Complement Concentration", pp. 379–382, 1989.

Tan et al., "Influence of the Hinge Region on Complement Activation, C1q Binding, and Segmental Flexibility in Chimeric Human Immunoglobulins", pp. 162–166, 1990.

Morrison et al.; Annals of the New York Academy of Sciences; vol. 507, pp. 187–198; 1988.

Bindon, et al.; Journal of Experimental Medicine; vol. 168, pp. 127–142; 1988.

*Primary Examiner*—George C. Elliott
*Attorney, Agent, or Firm*—Foley & Lardner

[57] ABSTRACT

The present invention provides modified IgG3 containing human constant regions which has a shorter total-hinge region compared with normal human IgG3. Also described is a method for assaying an antibody against a specific antigen or hapten for its effectiveness in complement activation in an animal species, wherein the antibody is contacted with the immobilized antigen or hapten to form an immobilized antibody/antigen or hapten complex which is then contacted with complement from the relevant animal species, followed by assay of components of the complement complex thereby formed; whereby the extent and nature of complement activation by the antibody in the sample may be determined.

14 Claims, 9 Drawing Sheets

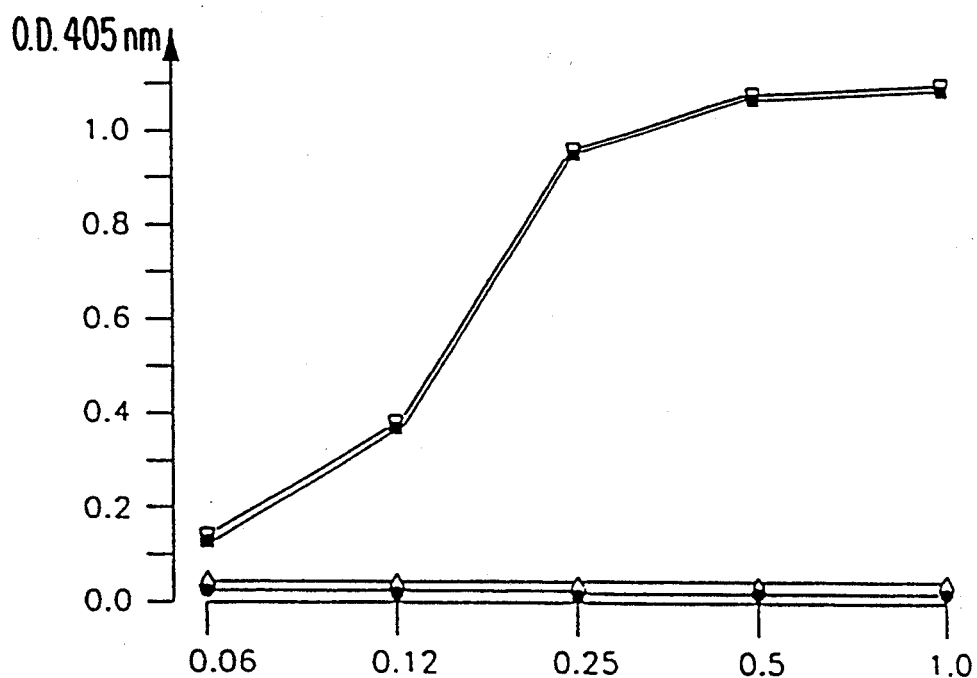
FIG. IIA
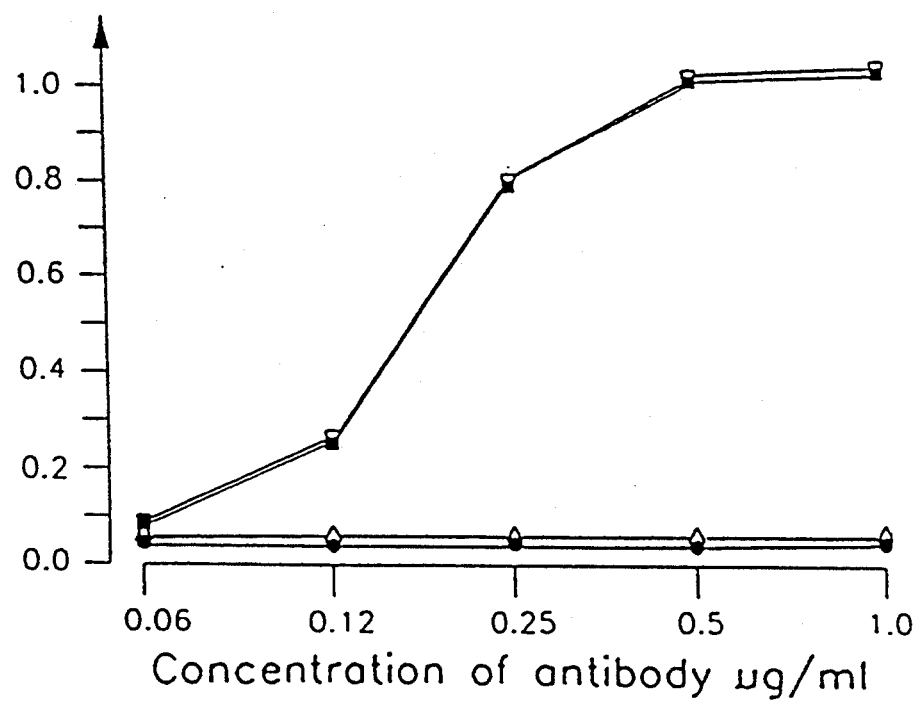
FIG. IIB
Concentration of antibody μg/ml

Concentration of antibody μg/ml

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 15 amino acids
( B ) TYPE: amino acid (D) TOPOLOGY: linear (xi) SEQUENCE DESCRIPTION: SEQ ID NO:1:

Glu Pro Lys Ser Cys Asp Thr Pro Pro Cys Pro Arg Cys Pro
1               5                   10                  15

(2) INFORMATION FOR SEQ ID NO:2:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:2:

Glu Pro Lys Ser Cys Asp Thr Pro Pro Cys Pro Ser Cys Pro
1               5                   10                  15

(2) INFORMATION FOR SEQ ID NO:3:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:3:

Glu Pro Lys Ser Cys Asp Cys Pro Ser Cys Pro
1               5                   10

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:4:

Glu Ser Lys Tyr Cys Asp Cys Pro Ser Cys Pro
1               5                   10

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:5:

Glu Pro Lys Ser Cys Asp Lys Thr His Thr Cys Pro Pro Cys Pro
1               5                   10                  15

(2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:6:

Glu Leu Lys Thr Pro Leu Gly Asp Thr Thr His Thr Cys Pro Arg Cys
1               5                   10                  15
Pro (2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( x i ) SEQUENCE DESCRIPTION: SEQ ID NO:7:

GACACAACTC ACACATGCCC                                                20

IGG3 ANTIBODIES WITH SHORTENED HINGE REGION AND A COMPLEMENT ACTIVATION TEST

This invention relates to modified IgG3 antibodies having human constant regions, and to a novel antibody assay system.

Human IgG consists of four subclasses which show 5% homology in the amino acid sequence of the constant domains of their heavy chains. However, the hinge regions of these molecules differ both in length and in sequence. The length of the hinge is 15 amino acids for IgG1, 12 amino acids for IgG2 and IgG4, while it is 62 amino acids for IgG3, and the sequence homology is approximately 60%. The hinge region of IgG3 is encoded by four exons separated by short introns, and consists of a NH$_2$-terminal 17 amino acid residue segment followed by a 15 amino acid residue segment which is consecutively repeated three times [1-3].

The subclasses show differences in effector functions, and it has been suggested that some of these could be due to differences in the flexibility of the antibody molecule, and that this in turn depends on the length of the hinge, as well as interplay between the first domain in the constant heavy chain ($C_H1$) and the hinge [3-7].

It has been shown, both with myeloma protein [8] and with a set of recombinant IgG molecules with identical V regions [3,9,10] that among the four IgGs, IgG3 is the most efficient in the first step of the classical complement activation pathway, namely Clq binding. Clq binding to the antibody is the first step in the complement cascade which leads to cell lysis. This effect or mechanism is of particular importance in combating microbial infection and has a role in the destruction of cancerous cells.

It is thought that the upper part of the hinge determines the flexibility of the Fab arms relative to one another, allowing rotation of the Fab arms [11]. This flexibility may facilitate efficient aggregation of antibody molecules on an antigenic surface with several epitopes, resulting in several Clq binding sites coming in close proximity and thereby increasing the affinity of Clq for antibody. The middle of the hinge contains cysteines (which participate in interchain disulphide bridges) and a high content of proline, and therefore probably adopts a relatively rigid structure, separating the Fab and Fc portions of the molecule.

In order to establish whether the efficient binding of Clq to human IgG3 is due to the structure of its particular hinge region, we have made genetically engineered chimetic IgG3 antibodies containing human constant regions, the hinges of which have been shortened and in which the amino acid sequence may have been altered.

Surprisingly, we found that where the amino acid composition of the hinge region was unmodified Clq binding was substantially independent of both the total hinge length and the length of the so-called upper hinge of IgG3. The upper hinge is defined as the stretch from the end of the $C_H1$ domain to the first inter-heavy chain disulphide bridge [12]. An IgG3 mutant with a hinge of 15 amino acids bound Clq just as efficiently as one with a hinge of 47 amino acids. Both these IgG3 variants bound more Clq than the wild-type, and much more than IgG1.

By modifying the amino acid sequence of the shortened hinge region however we have found that Clq binding, and thus complement mediated cytolysis can be further improved. In particular in IgG3 molecules having human constant regions, where the hinge region has been modified to approximate the sequence of a human IgG4 hinge region, improvements of up to 100 times greater complement-mediated cytolytic capacity have been obtained. Thus as little as 1/100th of the concentration of this mutant antibody is required to give 50% lysis of target cells, compared to the wild type.

A first aspect of our invention therefore provides modified IgG3 antibodies containing human constant regions which have a shorter total-hinge region compared with normal human IgG3.

The IgG3 may be modified by reducing the number of repeats of the 15 amino acid residue segment or by removing the 17 amino acid residue segment or a combination of these deletions. This produces what are referred to herein as "truncated variants". For example, the hinge region of such a truncated IgG3 variant according to the invention may consist of only one 15 amino acid residue segment.

The shortened IgG3 variants may also be modified by altering the amino acid sequence of one or more hinge region segments for example by substituting or deleting certain amino acids.

The modified IgG3 may be chimeric and may be expressed by monoclonal human hybridomas.

The use of monoclonal antibodies with defined specificity has been suggested for the detection and treatment of a variety of human diseases. For many reasons, human Ig is expected to be superior to mouse Ig in human therapy. Several groups have employed genetic engineering techniques to construct chimeric antibodies consisting of mouse variable regions joined to human constant regions [13-16]. Such antibodies have been shown to retain their antigen specificity while retaining the effector functions of the human antibody.

Accordingly, as a second aspect of the invention, we provide a chimeric IgG3 comprising variable antigen binding domains from a non-human species, a shortened total hinge region which optionally has been altered, and human constant regions.

A preferred method of obtention of modified IgG3 according to the invention involves the use of genetic engineering techniques although chemical modification may be possible. Genetic engineering involves the manipulation of nucleic acids which code for the IgG3 and can involve deletion of certain coding sequences, the combination of others, or amino acid deletion or substitution for example by site-directed mutagenesis. Genomic DNA for human IgG3, as for other IgG subclasses, consists of a number of exons and introns and the invention extends to modified DNA, with or without some or all of the introns, which DNA encodes modified IgG3 according to the invention. In addition to recombinantly modified DNA on sequences with amino acid substitutions or deletions, such DNA includes wild-type DNA lacking one, two or three exons coding for segments of the total hinge region. The invention also extends to RNA which codes for the modified IgG3 according to the invention. The invention also includes the modified DNA according to the invention when incorporated into a vector permitting expression in mammalian cell-lines and to such cell-lines when transfected with such vectors.

With regard to DNA coding for human IgG3 it is known that the hinge region is coded for by four exons h1 to h4 separated by three introns. These exons lie between the exons of the IgG3 gene which code for $C_H1$ and $C_H2$ domains; the latter being involved in complement fixation.

Preferred modified IgG3 molecules according to the invention include truncated variants where the hinge region has been reduced to a single repeat of the 15 amino acid sequence, and particularly those where, as indicated above, this 15 amino acid sequence has been modified by site-directed mutagenesis to resemble the human IgG4 hinge region sequence.

The preferred modified IgG3 molecules therefore have the following hinge region sequences:

(1) (SEQ ID NO:1) Glu-Pro-Lys-Ser-Cys-Asp-Thr-Pro-Pro-Pro-Cys-Pro-Arg-Cys-Pro
(2) (SEQ ID NO:2) Glu-Pro-Lys-Ser-Cys-Asp-Thr-Pro-Pro-Pro-Cys-Pro-Ser-Cys Pro
(3) (SEQ ID NO:3) Glu-Pro-Lys-Ser-Cys-Asp-Cys-Pro-Ser-Cys Pro
(4) (SEQ ID NO:4) Glu-Ser-Lys-Tyr-Cys-Asp-Cys-Pro-Ser-Cys Pro (m3)

Sequence (1) (SEQ ID NO:1) is the unmodified 15 amino acid sequence of human IgG3 and sequence (4) (SEQ ID NO:4) corresponds to the hinge region of human IgG4.

To evaluate the efficiency of Clq binding as a means of comparing the modified IgG3's of the invention we have developed a new assay system for antibodies, which however, can be usefully applied to any antibody.

When complement reacts with an antibody/antigen complex and is "activated", it triggers a cascade of reactions involving many components of the complement system, for example C1 (Clq), C3, C4, C5 and culminates in the formation of the TCC complex, the terminal (or "lyric") C5-9 complement complex which causes cytolysis to occur. Our new assay is based on the concept of contacting the antibody with the antigen and a complement preparation free from the relevant antibody, followed by assay of the amount of one or more such components, notably TCC, and forms a further aspect of the present invention.

Thus, according to a third aspect of the present invention we provide a method for assaying an antibody against a specific antigen or hapten for its effectiveness in complement activation in an animal species wherein the antibody is contacted with the immobilised antigen or hapten to form an immobilised antibody/antigen or hapten complex which is then contacted with complement from the relevant animal species followed by assay of components of the complement thereby formed and bound to the antibody/antigen or antibody/hapten complex, whereby the extent and nature of complement activation by the antibody in the sample may be determined.

When an aqueous sample, for example human serum, is tested quantitatively or qualitatively by conventional methods to determine the presence and the concentration of an antibody, for example after vaccination or exposure to infection, the result gives no indication of the effectiveness of the antibody, that is its ability to combat infection. Similarly a monoclonal antibody may show good antigen binding but be inefficient in complement activation and thus in antigen elimination.

Since one of the principle mechanisms whereby antibodies are able to eliminate foreign antigens is by activation of the complement system after binding to the antigen, the advantage of the new assay of the invention lies in enabling the effectiveness of an antibody in eliminating an antigen to be assessed, for example, the level of the immune response after initial vaccination or exposure to infection.

The antibody to be assayed will most commonly be present in a serum sample from a human or animal. As indicated below such serum may also serve as the source of complement. The invention thus provides a convenient and rapid method of assay of protective immunity which may be carried out, in many instances, under field conditions.

The method may be applied to a wide range of species including not only humans but animals such as domestic animals, and fish.

Although the assay according to the invention only directly measures complement activation by the antigen/antibody or hapten/antibody complex, it will be appreciated that this provides an indication of ability to effect lysis of cells carrying the antigen or hapten and also ability to effect phagocytosis by effector cells.

Thus in addition to proving useful in comparisons of modified antibodies, the antibody assay method according to the invention enables the efficiency of complement activation of an antibody to be compared with that of a standard, known antibody against the source antigen or hapten. This enables vaccines to be evaluated, the level of immune response of human and animals to be determined when exposed to infection and the mode of action of different antibodies against the same antigen to be investigated.

The complement components so immobilised can readily be assayed using available antibodies against each component, which antibodies may be labelled before or after binding. It is convenient to react unlabelled anti-complement antibodies, e.g. anti-Clq or anti-TCC from one animal, e.g. rabbit or mouse, and to label these subsequently by addition of anti-rabbit or anti-mouse antibodies conjugated to a label e.g. an enzyme such as horseradish peroxidase. The assay of the complement components may be effected directly on the immobilised material or in the fluid phase after liberation from the support, e.g. by proteolysis of protein binding the antigen or hapten to the support. Any method of immunoassay may be employed, including sandwich and competitive binding assays, using such labels as radionuclides, enzymes, dyes etc, in homogeneous or heterogeneous assay systems.

The support may take a number of forms. ELISA plates or microtitre wells may be used in the conventional way. Beads or particles also represent useful supports, particularly magnetic beads such as the monodisperse, supermagnetic beads sold by DYNAL AS (Oslo, Norway).

The complement source may conveniently be fresh serum, e.g. human serum where the antibody is a human antibody, or a chimeric antibody comprising a significant human region e.g. the constant region. Where the antibody under study is raised in vivo, the serum so obtained may serve as the source of both antibody and complement. It will be appreciated that complement activation will only begin when the antibody reacts with the immobilised antigen or hapten. The serum may be frozen at −70° C. immediately after blood-coagulation and thawed prior to use. Alternatively, the simplicity of the procedure enables the assay to be carried out on fresh serum under field conditions.

The immobilisation of the antigen permits thorough washing between each of the stages of antibody binding, labelling and assay.

It is desirable to run a control assay in parallel, using an inactivated sample of the serum used as source of the antibody and/or complement. Non-specific binding can be reduced by washing with a blocking agent such as gelatin or a non-ionic surfactant such as Tween 80.

The loading of the antigen on the support may influence the effectiveness of complement activation. A suitable loading can readily be determined by trial and error.

The immobilisation of the antigen or hapten may be effected by conventional methods. Where the antigen is a cell wall antigen, the whole cell may be bound to the immobilising support, e.g. via an antibody against a different cell-wall antigen, the antibody being bound covalently or by affinity to the support. Where the antigen is not bound to a cell, it may readily be bound covalently to the support using a conventional coupling agent. Similarly, a hapten may be immobilised by a suitable coupling agent binding to the support. A further possibility is to bind a second antibody or an antibody fragment, e.g. Fab'2 against the antigen or hapten to the support and to bind the antigen or hapten to this, thus providing a sandwich form of immobilisation. In the case of haptens, this permits liberation of the antibody by addition of excess hapten (or hapten analogue) and assay of the complement components bound to the antibody in the fluid phase.

This invention will now be described by way of non-limiting examples with reference to the drawings in which.

Figure 7:
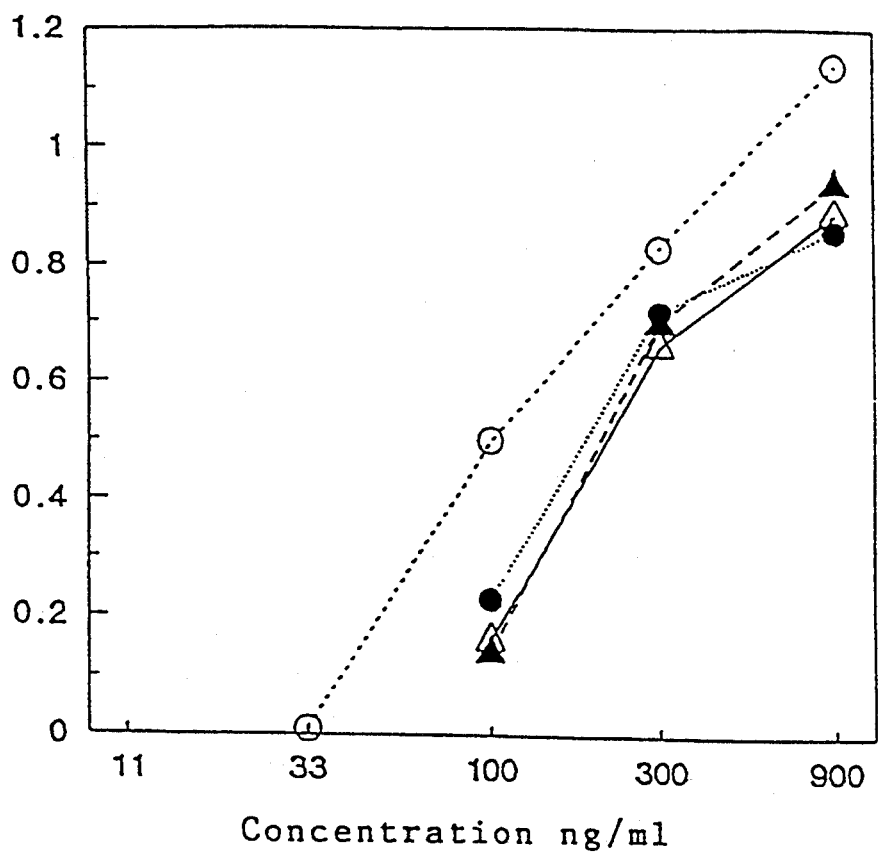
Figure 8:
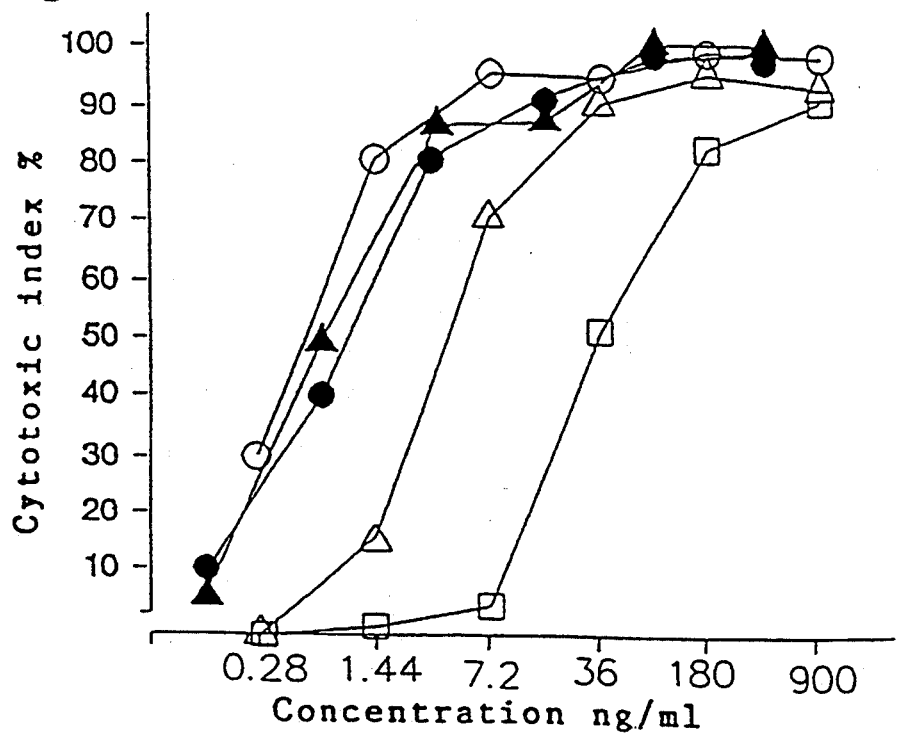
Figure 9:
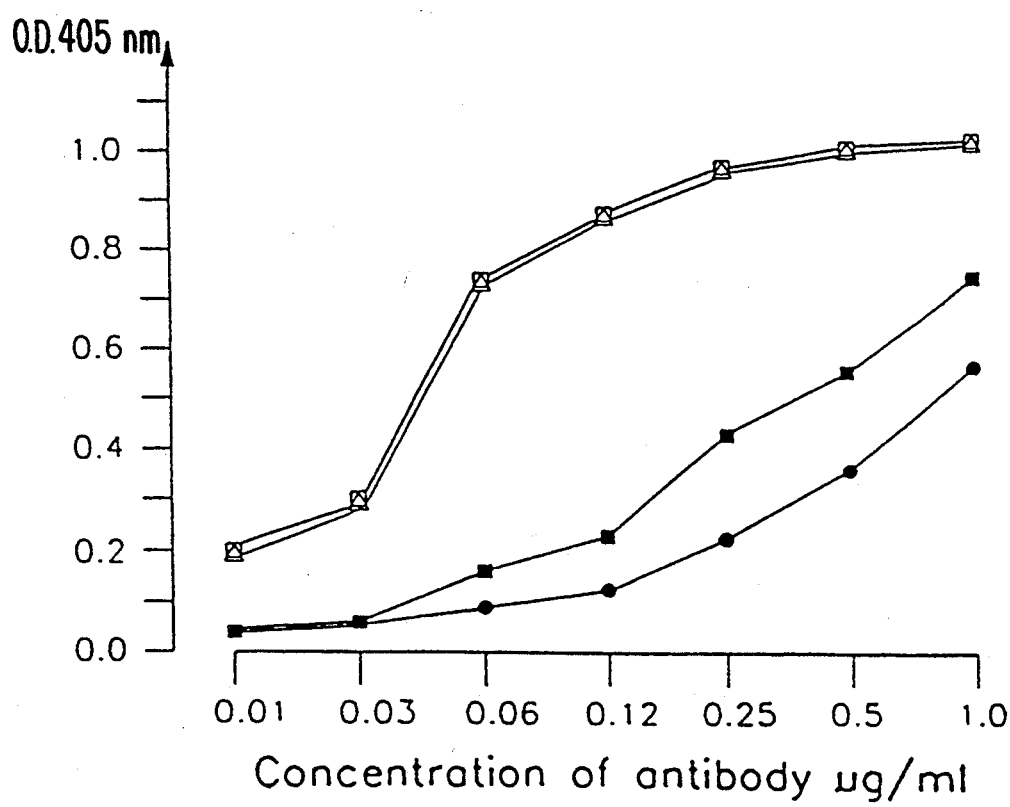
Figure 10:
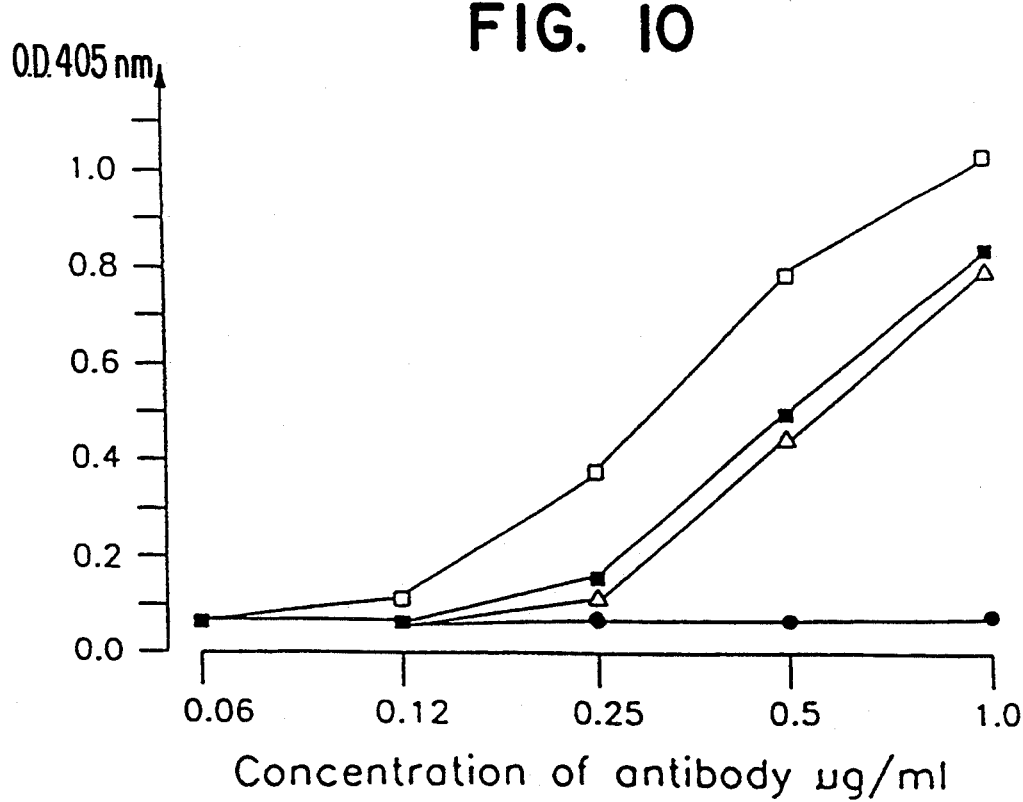

FIG. 7 shows graphically the level of complement activation obtained with site-directed IgG3 mutants. ELISA measurement of complement activation was revealed by developing with anti-Clq antiserum. The figure shows the dose response curves of the "origin" mutant 15 (△) and the three mutants, M1(○), M2(●) and M3(▲);

FIG. 8 graphically the level of complement mediated cytolysis associated with wild-type IgG3 (17-15-15-15) (□) and mutagenised IgG3 molecules (the "origin" mutant for site-directed maltagenesis (15) (△) and routants M1(○), M2(●) and M3 (▲);

FIG. 9 shows graphically the binding of IgG3 to solid phase absorbed antigen. Binding curves for the IgG3 anti-NIP antibody to solid phase absorbed NIP-BSA are shown after addition of normal serum (□), normal serum in EDTA-buffer (△), addition of NIP before normal serum (●), and addition of NIP after normal serum (■);

FIGS. 10 to 12 show the binding of complement components to antibody/antigen complexes, specifically:

FIG. 10 shows binding curves for Clq to anti-NIP/-NIP-BSA immune complexes. Optical density versus concentration of anti-NIP antibody. Symbols as described in FIG. 9.

FIG. 11A shows binding curves for C4and to anti-NIP/NIP-BSA immune complexes. Optical density versus concentration of anti-NIP antibody. Symbols as described in FIG. 9.

FIG. 11B shows binding curves for C3 to anti-NIP/-NIP-BSA immune complexes. Optical density versus concentration of anti-NIP antibody. Symbols as described in FIG. 10.

Figure 12A:
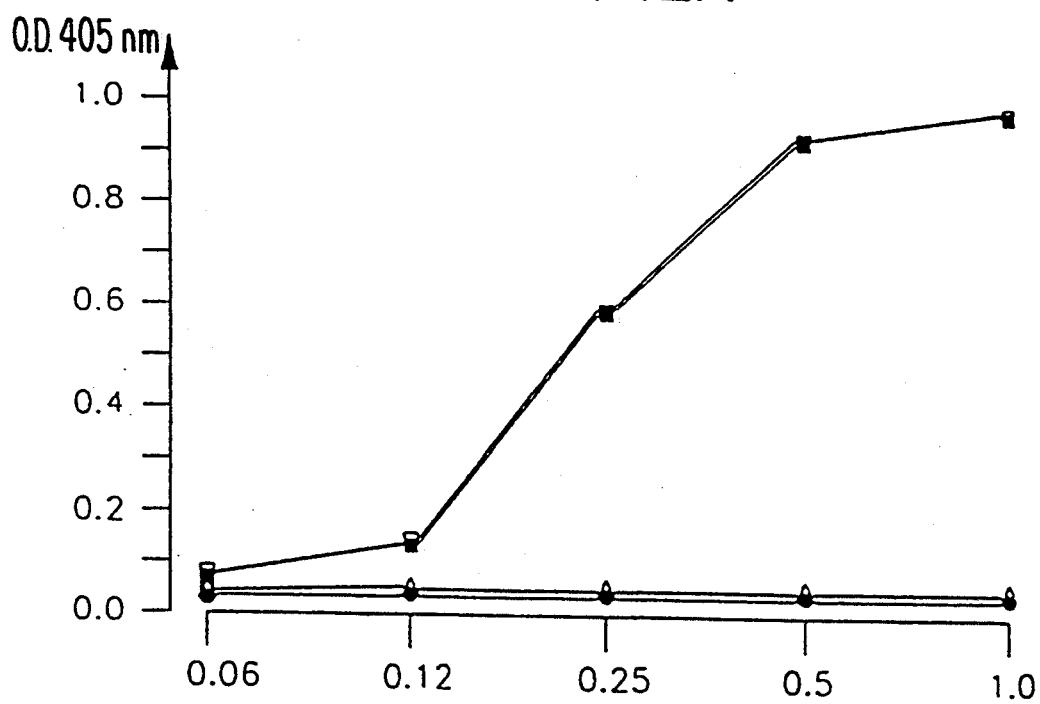

FIG. 12A shows binding curves for C5 and the to anti-NIP/NIP-BSA immune complexes. Optical density vs concentration of anti-NIP antibody. Symbols as described in FIG. 9.

Figure 12B:
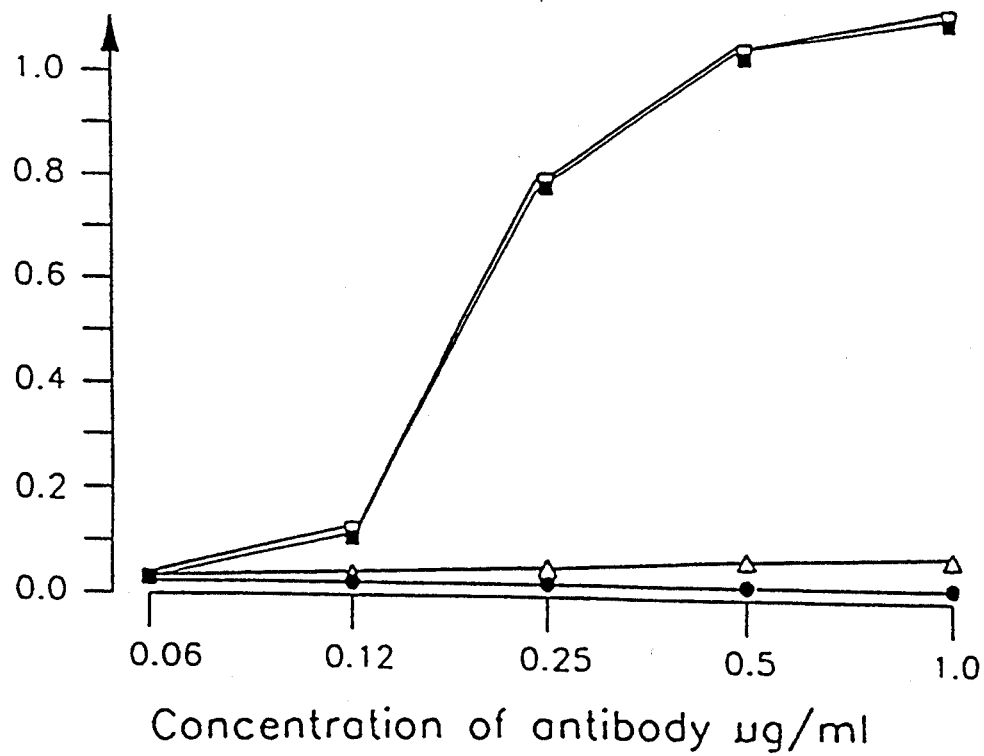

FIG. 12B shows binding curves for the C9 neo-epitope to anti-NIP/NIP-BSA immune complexes. Optical density versus concentration of anti-NIP antibody. Symbols as described in FIG. 10.

Figure 13:
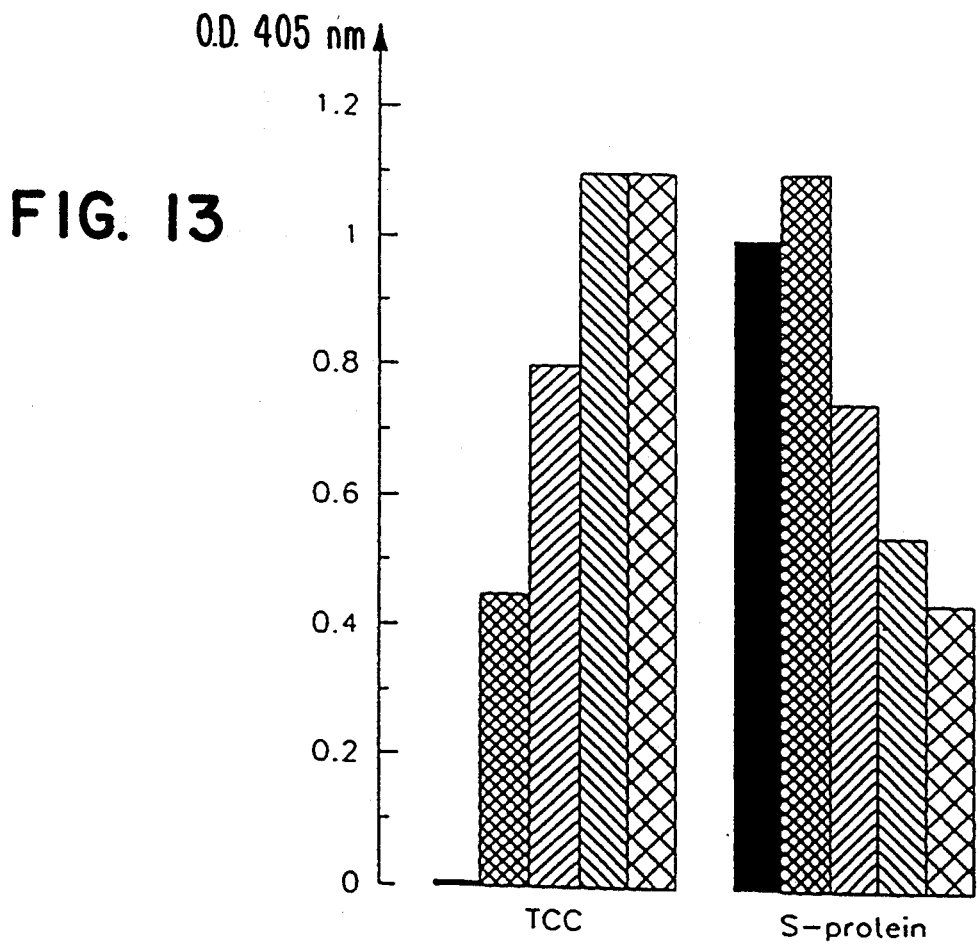

FIG. 13 shows the effect of increasing antigen concentrations on ICC formation. To the left is shown the binding of the TCC with increasing amounts of NIP-BSA as target for the chimetic antibody (concentration of 1 $\mu g/ml$). To the right is shown the binding of the S-protein/vitronectin in a parallel experiment. In the figure

| ■ | represents | 0 $\mu g/ml$ NIP/BSA, |
| ⊠ | | 1 $\mu g/ml$ |
| ▨ | | 10 $\mu g/ml$ |
| ▩ | | 100 $\mu g/ml$ |
| ⊠ | | 1000 $\mu g/ml$ |

Figure 15:
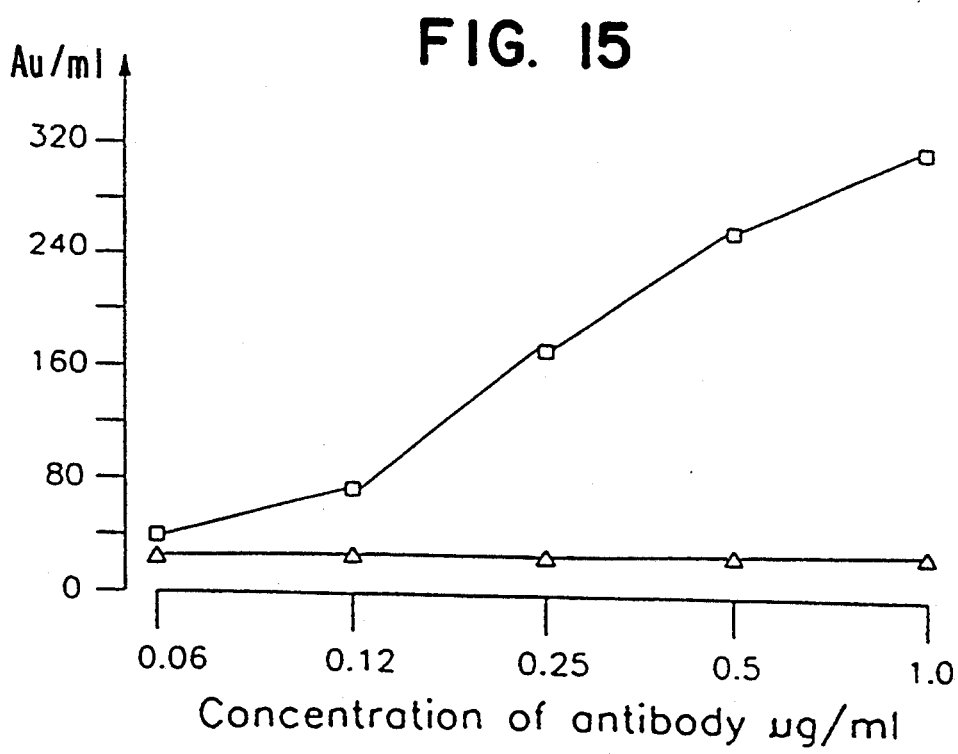
Figure 14A:
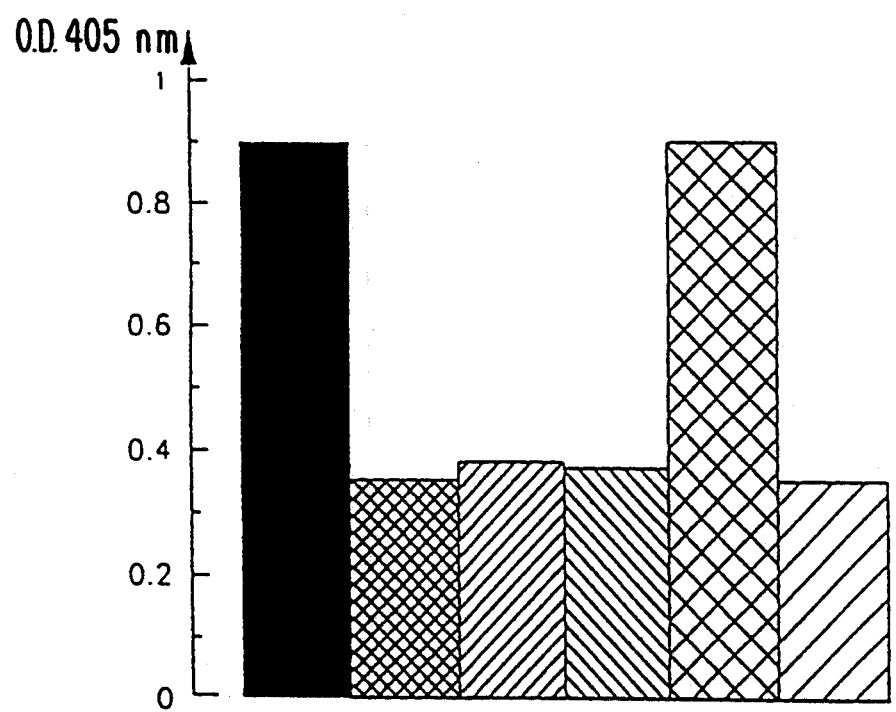
Figure 14B:
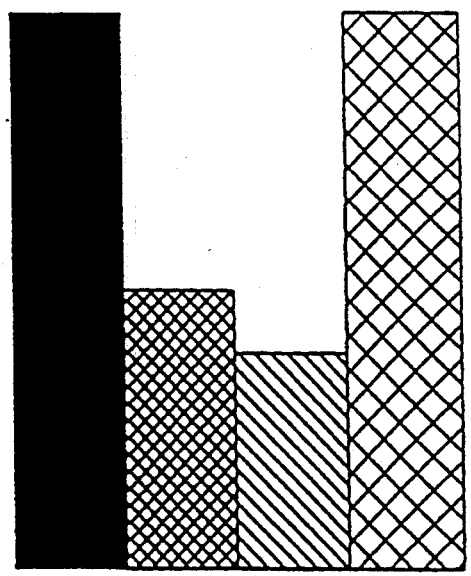

FIG. 14 shows the complement binding of antibody/antigen complexes in a sandwich assay. Binding of TCC in a sandwich immune complex assay by using NIP-BSA as Ag is shown. Solid bar indicates binding in the presence of NIP-BSA. Narrow cross-hatched bar indicates all steps except NIP-BSA. Narrow right hatched bar indicates EDTA control. Narrow left hatched bar indicates binding in the presence of pepsin. Wide cross-hatched bar indicates binding in the presence of pepsin buffer without pepsin. Wide right hatched bar indicates omission of the anti-C9 neo-epitope mAb, and FIG. 15B shows the complement binding of antibody/antigen complexes in a sandwich assay. Binding of BSA in a sandwich immune complex assay by using NIP-BSA as Ag is shown. Solid bar indicates binding in the presence of NIP-BSA. Narrow cross-hatched bar indicates all steps except NIP-BSA. Narrow left hatched bar indicates binding in the presence of pepsin. Wide-crossed hatched bar indicates binding in the presence of pepsin buffer without pepsin; and FIG. 15 shows fluid phase activation and TCC formation. Fluid phase C3 activation (Au/ml) vs concentration of anti-NIP antibody is shown. Supernatants obtained from the solid phase C activation assay shown in FIGS. 10, 11, and 12 were tested for C3 activation products. Symbols as described in FIG. 9.

EXAMPLE 1

Materials and Methods

1. Immunological reagents. Anti-Clq was supplied by Daco (Copenhagen, Denmark). All the other antibodies and conjugates were made in our laboratory.

2. Buffers

Isotonic veronal-buffer (IVB) at pH 7.3 was prepared with 1 mM $MgCl_2$ and 1 mM $CaCl_2$.

3. Cloning procedures and gene mapping.

The human γ3 constant region gene used in this study codes for a G3m(b°) variant [2] generously provided by Dr. M. P. Lefranc (Laboratoire d'Immunogenetique, Universite des Sciences et Techniques du Languedoc, France). The construction of the mutant Cγ3 genes will be described later. They were subsequently cloned into a pSV2gpt plasmid vector containing a variable murine heavy-chain region gene, pSV-$V_{NP}$ [10] thus creating complete γ3 heavy chain genes. The $V_{NP}$ gene segment codes for a variable heavy chain characteristic of λ1 light chain bearing mouse antibodies with specificity for the hapten 4-hydroxyl-3-nitrophenyl acetic acid (NP) and also binds to the hapten analogue NIP (5-iodo-4-hydroxy-3-nitrophenyl acetic acid) [17]. pSV-$V_{NP}$ was a gift from Dr. M. S. Neuberger (Medical Research Council Laboratory of Molecular Biology, Cambridge, England).

The mutant Cγ3 genes were analysed for the presence of the first hinge exon, h1, by dot-blotting as follows: Samples of 0.5 μg plasmid DNA were spotted on a nylon membrane, and subjected to hybridization with a h1 specific synthetic probe. This deoxynucleotide (SEQ ID NO: 7), 5'-GACACAACT-CACACATGCCC-3', was made by the phosphoramidite method on an Applied Biosystems DNA synthesizer model 381A. Before hybridization the probe was 5'-labelled with 32p ATP. Hybridization was for 16 hours in 6×SSC AT 57° C.

The filter was washed in 6×SSC, 0.1% SDS for 1 hour at 57° C. followed by 1×SSC, 0.1% SDS for 1 hour at room temperature.

The recombinant DNA work was performed by standard procedures [18].

3.1. Cell growth and gene transfer.

J558L is a murine myeloma cell line which secretes a l light chain, but does not produce any immunoglobulin heavy chain [19]. The cells were obtained from Dr. S. L. Morrison (Dept. of Microbiology, College of Physicians and Surgeons, Columbia Univ., New York). They were grown in Dulbecco's modified Eagle's medium with 10% fetal calf serum supplemented with 2 mM glutamine, 1 mM sodium pyruvate, 50 IU/ml penicillin, 50 μg/ml streptomycin, and 100 μg/ml gentamicin sulfate (all from GIBCO).

pSV2gpt vectors containing complete mutant immunoglobulin heavy chain genes (pSV-$V_{NP}$Cγ3ΔPstI) were transfected into J558L cells by electroporation [20]. Approximately $10^7$ cells and 20 μg plasmid in 0.8 ml of PBS at 6° C. were subjected to an electric field of 3.5 kV/cm using a capacitance setting of 25 μF. The DNA was linearized at the PvuI site within the pBR322 sequence prior to electroporation. After incubation at 37° C. for 48 hours in growth medium, the cells were transferred to growth medium supplemented with 1 μg/ml mycophenolic acid (GIBCO) and 250 μg/ml xanthine to select for transfected cells. Clones were visible after 1-2 weeks. Individual clones were selected by limiting dilution.

3.2. Quantification of secreted Chimeric IgG3.

The amount of IgG3 secreted by transfectants was measured by a catching ELISA method. Microtitre plates (Nunc) were coated with affinity purified sheep anti-human IgG which reacts equally well with all IgG subclasses. After being left overnight 4° C., the plates were washed with PBS/0.05% Tween 20 (PBS/T). Sample of 150 μL cell supernatant supplemented with Tween 20 to a final concentration of 0.05%, were added to the wells and incubated at 37° C. for 2 hours. The next layer consisted of biotin-labelled sheep anti-human IgG or IgG3 (hinge specific) mixed with streptavidin-alkaline phosphatase made by the one step glutardialdehyde method [21]. The anti-IgG antibodies were diluted 1:4000, and the streptavidin-alkaline phosphatase 1:6000 in PBS/T. After a 2 hour incubation at 37° C. the wells were washed and the substrate NPP added. The plates were incubated at 37° C. for 30 min before absorbance at 405 nm was measured using an ELISA reader (Dynatech MR 500). Standard curves were constructed by measuring the absorbance of serial dilutions of purified IgG3 myeloma proteins. The method accurately measured antibody concentrations in the range from 10 ng/ml to 1 μg/ml.

3.3. Hapten labelling of BSA

BSA was labelled with NIP by using NIP-caprylate-o-succimidylester (Cambridge Research Biochemicals, Cambridge, England). To one ml of 20 mg/ml BSA (Behring, Marburg, F R G) dissolved in 0.1M $NaHCO_3$ pH 8.5 with 0.15M NaCl was added 200 μl 20 mg/ml NIP-Cap-O-Su in dimethylformamide and left at room temperature for 2 hours before the addition of 100 μl 1M ethanolamine pH8.5 and dialysed over night against PBS pH7.3 with 0.02% $NaN_3$. The NIP:BSA molar ratio was calculated to be 54:1 by measuring absorbance at 405 nm and at 280 nm.

3.4. Clq binding assay

The Clq binding activity of the different chimeric antibodies was measured as will be fully described below. Briefly, microtitre plates were coated with BSA-NIP (150 μl, 1 μg/ml), washed, and serial dilutions of chimeric antibodies were added to the wells. 1:20 diluted normal fresh serum was used as diluent. After 1 hour at 37° C. the plates were washed and rabbit anti-Clq (Daco, Denmark) 1:2000 diluted in PBS/T was added to each well. The plates were incubated at 37° C. for 2 hours, washed again and a mixture of biotinylated sheep anti-rabbit IgG and Streptavidin-alkaline phosphatase conjugate made by the glutardialdehyde method was added. After another incubation at 37° C. for 2 hours the plates were washed, and bound Clq was revealed by addition of the substrate NPP (Para-nitrophenylphosphate). The reaction was carried out for 30-60 min at 37° C. before the plates were read at 405 nm in a microplate reader.

4. Results 4.1 Construction of human γ3 constant region deletion mutants.

Figure 1:
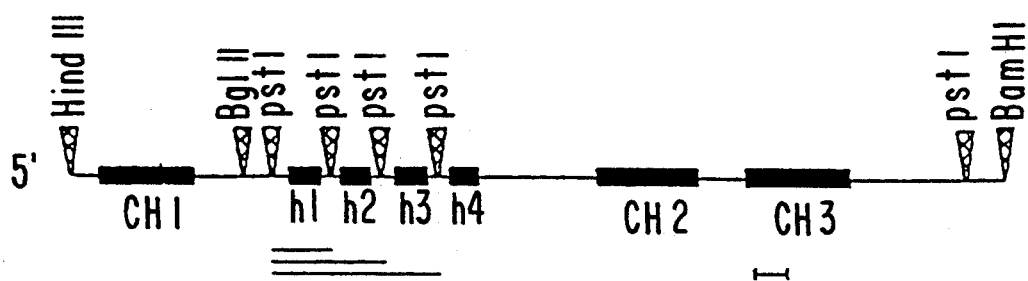
FIG. 1 shows a gene map for IgG3 (heavy chain)

The full length Cγ3 gene is contained on a 2.6 kb HindIII, SphI fragment cloned into the polylinker of pUC19. This plasmid was subjected to partial digestion with the restriction enzyme PstI. Each of the four hinge exons has a PstI site in the intervening sequence immediately upstream of its coding region (FIG. 1). The digested plasmid was run on an 0.8% agarose gel, and linearized plasmid of approximately 5 kb was isolated from the gel, ligated and introduced in *E. coli* JM85. Plasmid preparations of individual colonies were analyzed by digestion with appropriate restriction enzymes. Deletion mutants that had lost one, two or three hinge exons while retaining the remaining coding sequences intact were thereby identified (FIG. 1). Since the digested plasmid was size fractionated on an agarose gel before ligation, "shuffling" of the hinge exons was an unlikely event.

To test whether the deletion mutants contained the large 17 amino acid hinge segment, h1, samples of plasmid DNA were spotted on nylon membrane and hybridized to a $^{32}p$ end-labelled synthetic oligonucleotide probe, complementary to the h1 sequence.

Wild-type Cγ3, one mutant containing two hinge exons and three mutants containing three hinge exons hybridized with the probe, and hence carry the exon coding for the 17 amino acids hinge segment in addition to exons coding for the 15 amino acid segments. These mutant genes should code for constant heavy chains with hinge segments of 32 and 47 amino acids respectively. The plasmid containing a Cγ3 with only one hinge exon did not hybridize with the probe, as this exon is certainly h4, which codes for a 15 amino acids hinge segment. Also, one of the mutants containing three hinge exons did not hybridize with the probe. This gene has lost its large hinge exon, and consequently has three identical hinge exons each coding for a 15 amino acid segment, and should give rise to a heavy chain with a hinge segment of 45 amino acids.

4.2 Construction and transfection of complete chimeric mouse/human heavy chain games.

Figure 2:
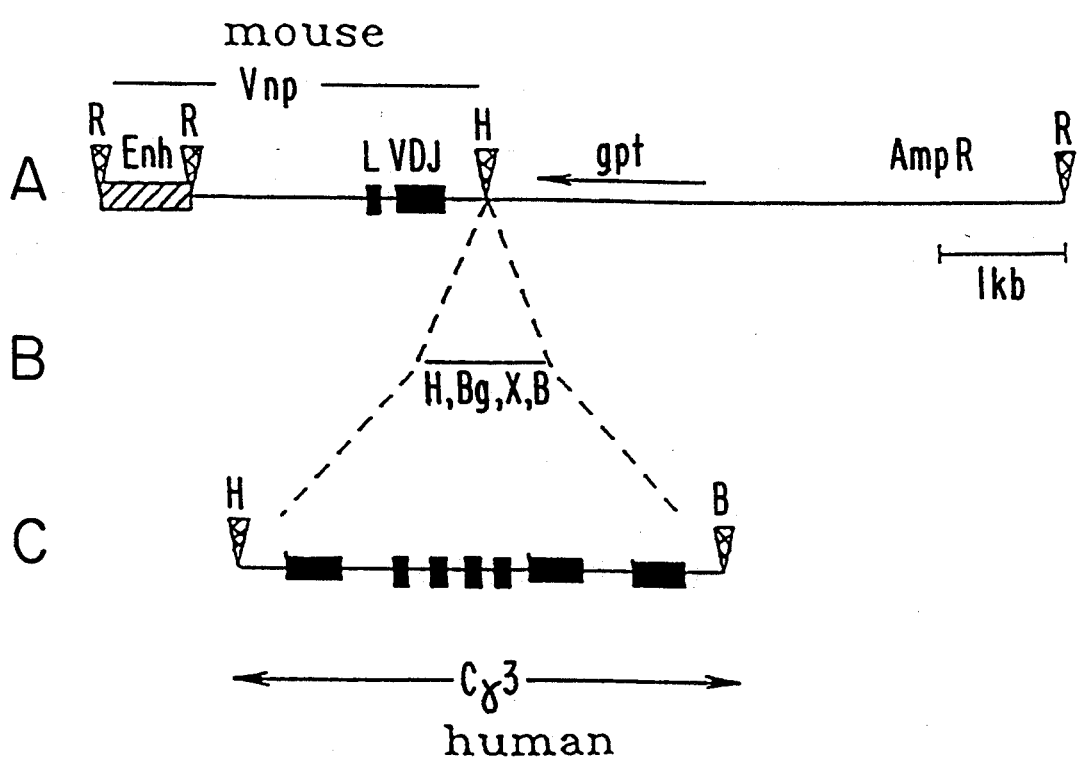
FIG. 2 shows a gene map for a chimeric IgG3 according to the invention.

The mutant Cγ3 genes (Cγ3ΔPstI) were introduced in a derivative of the selectable shuttle vector pSV2gpt [22]. This vector, called pSV-V$_{NP}$ [10] (FIG. 2*a*) contains a mouse variable region gene in addition to regulatory sequences for immunoglobulin gene expression in lymphoid cells. The transcription enhancer element (hatched area), which normally lies between V$_H$ and C$_H$, has been removed and inserted upstream of the variable gene segment. It has previously been shown that the enhancer is active on the V$_{HP}$ promoter at this position [17]. Downstream of the variable gene a polylinker in the HindIII site was introduced (FIG. 2*b*). The polylinker was introduced in the Hind III site of pSV-V$_{HP}$ in such a way that the Hind III site at the 3' end was destroyed. Restriction enzyme cleavage sites are shown as: B, Bam HI; Bg, Bgl II; H, Hind III; R, Eco RI; X, Xba I. The various Cγ3ΔPstI genes were removed from pUC19 and inserted into the polylinker on HindIII, BamHI fragments, thus complete chimetic immunoglobulin heavy chain genes (V$_{HP}$Cγ3ΔPstI) were made (FIG. 2*c*).

The heavy chains encoded by these genes in combination with the λ1 light chain expressed by the J558L myeloma, produce antibodies specific for the hapten NP. Thus, the various pSV-V$_{HP}$Cγ3ΔPstI plasmids were introduced in J558L cells by electroporation. The transfection efficiency was between $10^{-3}$ and $10^{-4}$ in different experiments.

Figures 3, 4:
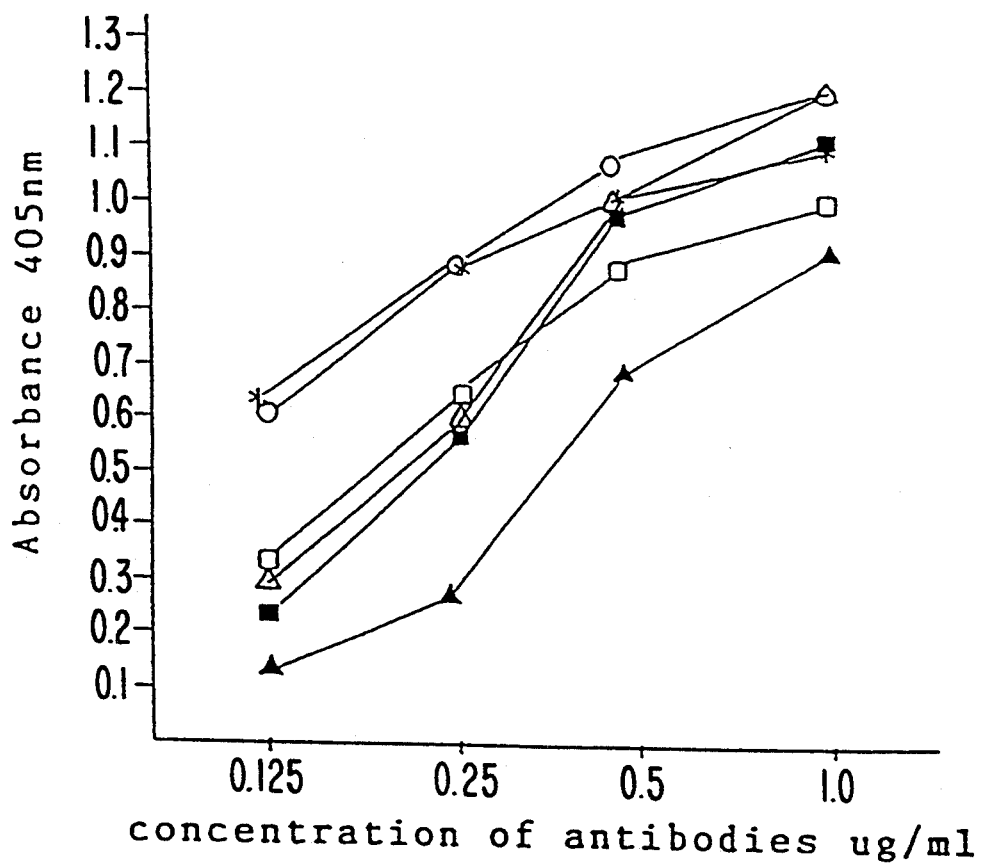
FIG. 3 shows graphically the Clq binding of various IgG3 and IgG1 molecules ((□) 17-15-15-15, (*) 17-15-15, (△) 17-15, (○) 15, (■) 15-15-15, and (▲) IGgl)
FIG. 4 shows amino acid residue sequence data for three different hinge regions (SEQ ID NOS 5,1, and 6 respectively)

FIG. 4 shows schematically wild-type IgG3 and four modified hinge region IgG3 molecules formed by PstI digestion and expressed in J558L cells, as described above.

4.3 Quantification and serological characterization of chimeric antibodies.

Culture supernatants of individual transfectants were assayed for production of chimeric IgG3 antibodies by an ELISA method using polyspecific anti-IgG antibodies. The antibody yields were 2–10 μg/ml.

All mutants reacted with both polyclonal and monoclonal IgG3 hinge specific antibodies. This result was also confirmed by ELISA inhibition experiments. Thus the basic hinge antigenic structure was conserved in the mutant molecules.

4.4 Binding of C1q.

Figure 6:
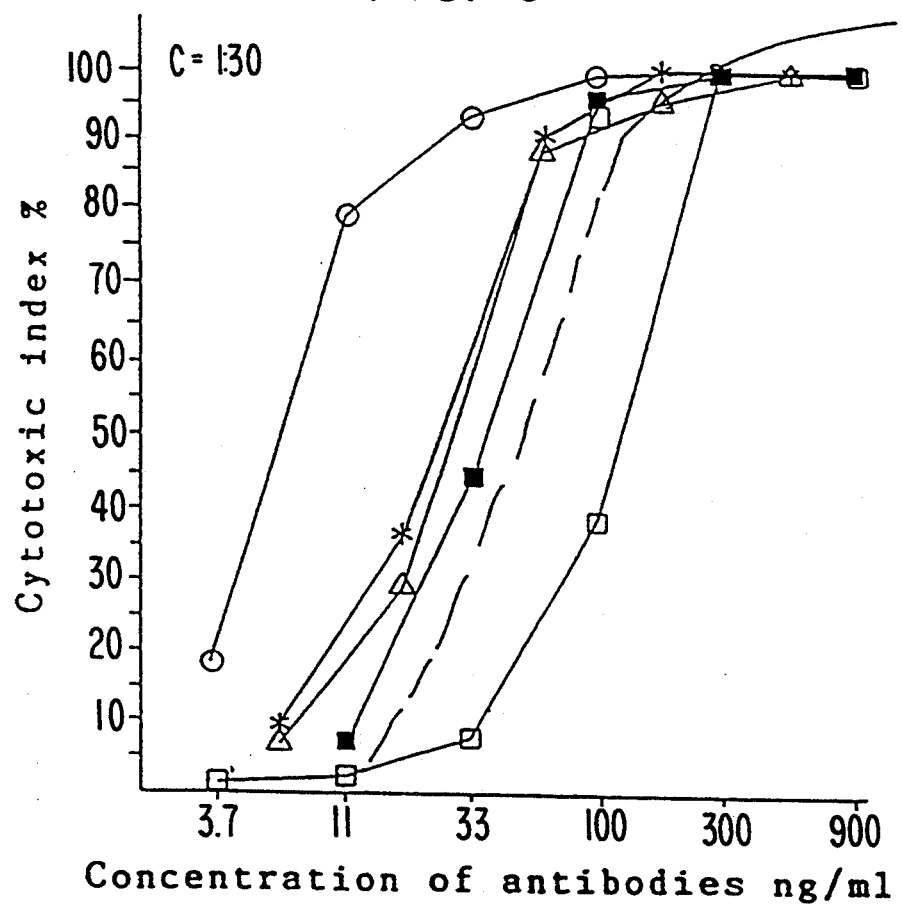
FIG. 6 shows graphically the level of complement mediated cytotoxicity associated with IgG3 and IgG1 molecules ((□) 17-15-15-15, (*) 17-15-15, (△) 17-15, (○) 15, (■) 15-15-15, and - - - IGgl)

The C1q-binding activity of the four mutant variants were tested in an ELISA assay and compared with wild-type IgG3 and IgG1 with the same variable region in parallel experiments (FIG. 3). In order to verify equal quantities of antibodies were used, parallel wells with the same dilution of chimeric antibodies were assayed by adding biotin-labelled anti-human IgG and streptavidin-alkaline phosphatase and developed as described in section 3.2. The dose response curves of all the subclasses were parallel and superimposable demonstrating the same quantity of all the subclasses was present in each case. Wild-type IgG3 was found to bind C1q more efficiently than IgG1. Surprisingly, all the truncated IgG3 mutants were at least as efficient as the wild-type IgG3 in C1q binding. We also found that the most truncated IgG3 variant with only one 15 amino acid hinge segment bound more C1q than IgG1, which also has a 15 amino acid hinge segment as shown in FIG. 6.

FIG. 4 shows a comparison of hinge sequences of wild-type human IgG with 15 mer and 17 mer modified hinge region IgG3 molecules. The first cysteine participating in interchain disulphide bridging is marked by an asterix thus showing the end of the upper hinge [12].

We have made recombinant IgG3 antibodies with shortened hinge regions and measured how hinge length correlates with binding of the complement component C1q. The antibodies have murine V$_{HP}$ heavy chain region, and human heavy chain constant regions. The corresponding λ1 light chain is expressed by the recipient murine cell line, J558L. Other groups have shown that it is possible to "humanize" murine antibodies in this way, and that chimeric antibodies secreted from J558L cells behave like their human counterparts in SDS-PAGE analysis, binding to protein A and a series of serological assays, in addition to showing human effector functions [3,9,10].

The mutant IgG3 molecules were recognized by both polyclonal and monoclonal IgG3 hinge specific antibodies, indicating that the basic hinge antigenic structure was conserved in the mutant molecules. The mutant antibodies all had the same variable region. this suggests that the effect of shortening the hinge can be studied independently of any effects due to difference in antigen specificity and affinity.

Our results confirm that wild-type IgG3 binds C1q more effectively than IgG1 [3,8]. Surprisingly C1q binding was found to be independent of IgG3 hinge length. All the mutants with shortened hinge were as efficient, or even more efficient than the wild-type in C1q binding.

Figure 5:
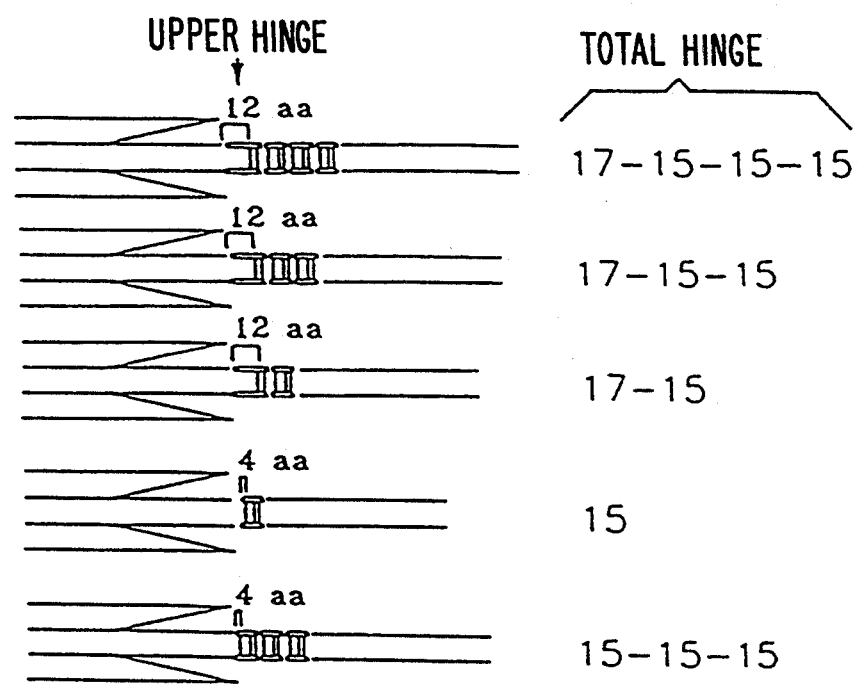
FIG. 5 is a schematic drawing showing five different IgG3 molecules.

In the h1 segment of IgG3 the upper part of the wild-type hinge consists of 12 amino acids and this might allow a greater flexibility than the corresponding hinge of IgG1 which is 10 amino acids long (FIG. 5). However, two of the IgG3 variants have upper hinges of only 4 amino acids, namely the one with a 15 amino acids hinge segment and the one with a 45 amino acids hinge segment. Both these variants showed C1q binding at least as effective as the wild-type IgG3. Consequently, Clq binding is independent both of the length of the upper hinge and the length of the middle hinge.

We have also found that not only do modified IgG3 molecules according to the invention give enhanced Clq binding but that complement mediated cytotoxicity is also enhanced up to 20-fold as shown in FIG. 6.

EXAMPLE 2

Methods

The method of site directed mutagenesis according to Kunkel was followed (T. A. Kunkel. Rapid and efficient site-specific mutagenesis without phenotypic selection. proc. natl. Acad. Sci. U.S.A., 82:488–492, 1985). A 1.37 kb Pst I gene fragment containing sequences encoding the h4, CH2 and Ch3 regions of IgG3 chains was subcloned in M13 mp 19. Single stranded template DNA was prepared from recombinant phage that had been propagated in the E. coli strain CJ236 which is dut-ung- and therefore substitutes dUTP for dTTp in DNA. In vitro mutagenesis was performed by annealing an 24–29 base long synthetic oligonucleotide (made by the phosphoramite method on an Applied Biosystems (Foster City, Calif.) DNA synthesizer model 381A) coding for the desired mutant amino acid sequence to the single stranded template DNA and preparing covalently closed circular double stranded DNA by incubating with T4 DNA polymerase and T4 DNA ligase in an appropriate buffer containing the four dNTP's. The double stranded DNA product was introduced in MV1190, a bacterial strain which is dut$^+$ ung$^+$, and therefore degrades the uridine containing template DNA, which codes for the wild type sequence. The in vitro synthesized DNA containing the mutant sequence, served as template for new phage DNA synthesis in MV1190. Single stranded and double stranded phage DNA was prepared from MV1190. The mutants were analyzed by DNA sequencing. Only the planned mutations were obtained. The mutant gene fragments were subcloned in pSV-V$_{np}$ as described in Example 1 for the hinge truncated mutants.

Results

Modified IagG3 molecules having the following hinge region sequences were obtained:

(1) (SEQ ID NO:1) Glu-Pro-Lys-Ser-Cys-Asp-Thr-Pro-Pro-Pro-Cys-Pro-Arg-Cys-Pro (origin)
(2) (SEQ ID NO:2) Glu-Pro-Lys-Ser-Cys-Asp-Thr-Pro-Pro-Pro-Cys-Pro-Ser-Cys Pro (M1)
(3) (SEQ ID NO:3) Glu-Pro-Lys-Ser-Cys-Asp-Cys-Pro-Ser-Cys Pro (M2)
(4) (SEQ ID NO:4) Glu-Ser-Lys-Tyr-Cys-Asp-Cys-Pro-Ser-Cys Pro (M3)

Sequence (1) (SEQ ID NO:1) corresponds to a single repeat of the unmodified 15 amino acid segment of the IgG3 hinge and is the "origin" sequence for the site-directed mutagenesis procedure. Sequences (2) to (4) (SEQ ID NOS 2 to 4, respectively) are the hinge region sequences of the site-directed mutants, sequence (4) corresponding to the hinge region sequence of IgG4.

Biological activity of the site directed hinge mutants

The mutants were tested for complement activation activity as described in Example 1 and the results are shown in FIGS. 7 and 8.

As can be seen in FIG. 7, the site-directed mutants M1 to M3 are slightly more active than the mutant carrying the "origin" sequence. When these mutants were tested for capacity to induce complement mediated cytolysis, the site-directed mutants were all better than the "origin" mutant and in particular the mutant M1 was particularly active (FIG. 8). This mutant was about 5× more active than the origin mutant, which on the other hand was up to 20× more active than the IgG3 wild type. The first site directed mutant (M1) is therefore expected to be about 100× more active in inducing complement cytolysis than the IgG3 wild type.

EXAMPLE 3

Materials and Methods

Antibody preparations. The following polyclonal rabbit antisera against human complement proteins were used: anti-Clq, anti-C1, anti-C3d and anti-C5 from Dakopatts, Copenhagen, Denmark and anti-C3e from Behringwerke AG, Marburg, FRG. The mouse monoclonal antibodies aE11 against a C9 neoepitope expressed on TCC, and bH6 against a C33 neoepitope on C3b, iC3b and C3c were produced as described by Mollnes et al. in Scand. J. Immunol 22 183 and Garred et al. in Scand. J. Immunol 27 319, respectively. Mouse monoclonal anti-body against S-protein/fibronectin was provided by Cytotech, San Diego, Calif., U.S.A. Peroxidase conjugated antirabbit Ig and anti-mouse Ig were obtained from Amersham International, Bucks., U.K. The construction and production of the chimeric human-mouse IgG3 against NIP have been described in detail in Neuberger et al. (Nature 1984). The chimeric antibodies were purified from culture supernatants by affinity chromatography. The affinity column was made by adding 10 ml AH Sepharose (Pharmacia, Uppsala, Sweden) washed with cold 3% (w/w) NaHCO$_3$ and suspended in 25 ml cold 3% NaHCO$_3$ to 20 mg NIP-caproate -O-succinimide. (Cambridge Research Biochemicals, Cambridge, U.K.) dissolved in 1 ml dimethylformamide (Pierce, Oud-Beijerland, Netherlands). The mixture was rotated head over head at 4° C. overnight and washed with phosphate-buffered saline (PBS), pH 7.3 until the effluent had no absorption at 280 nm. Free NIP in excess was used as eluent. The hapten was removed from the antibodies by extensive dialysis against PBS.

The specificity of all the polyclonal anti-complement antibodies was tested in sodium dodecyl sulphate-polyacrylamide gel electrophoresis (SDS-PAGE) with subsequent western blot analysis. It was revealed that the anti-C4, anti-C3 and anti-C5 antisera had some activity against IgG. This was further tested in the present assay by omitting the complement source. The influence of the anti-Ig activity was successfully abolished by adding human IgG (Kabivitrum, Stockholm, Sweden) to the anti-complement antibody buffer. In crossed immunoelectrophoresis the precipitation lines were found in characteristic positions.

Preparation of NIP-BSA. The NIP hapten was coupled to BSA by mixing 200 μl at 0.5 mg/ml NIP-capioate-O-succinimide with 2 ml 10 mg/ml bovine serum albumen (BSA Behring) dissolved in 0.1M NaHCO$_3$ and 0.5M NaCl pH 8.5. The mixture was left at room temperature for 2 hrs, then 0.5 ml 1M ethanolamine pH 8.5 was added and the solution was dialysed overnight against PBS pH 7.3 with 0.02% NaN$_3$.

Solid phase complement activation enzyme immuno assay. Polystyrene plates (Nunc immunoplate II, Teknunc, Copenhagen, Denmark) were coated with 100 μl of 1 μg/ml of NIP conjugated BSA at room temperature overnight. In TCC and S-protein experiments 10 μg/ml, 100 μg/ml, and 1 mg/ml NIP-BSA were also used. The chimeric IgG3 antibody diluted in PBS with 0.2% Tween 20 in appropriate concentrations (0.062–1.00 μg/ml) was then added. Normal human serum was used as the complement source; the serum was frozen immediately at 70° C. after coagulation and after thawing the serum was diluted to a final concentration of 1% in veronal buffered saline (VBS) with 0.2% Tween 20 and added to the wells. In the subsequent steps anti-complement antibodies in appropriate dilutions were used to detect complement deposits. Finally, perokidase conjugated anti-rabbit or anti-mouse IgG was used. Each step was incubated at 37° C. for 1 h. Between each step the polystyrene plates were washed extensively in phosphate buffer saline with 0.1% Tween 20, Substrate was 2,2'-azido-di-3-ethyl-benzthiazoline sulphonic acid (Boehringer, Mannheim, FRG) and the results were read on Dynatech MR 580 at 405 nm. Parallel experiments to control the chimeric antibody binding were performed with peroxidase conjugated anti-human Ig. Further control experiments were performed with 10 mM ethylene diamine tetraacetic acid (EDTA) in the complement buffer or inactivated serum heated at 56° C. for 30 min. Additionally, 0.2 mM NIP was added at different incubation steps in order to elute the chimeric antibody. The displacement of IgG in the presence of free NIP was calculated by using the diminished absorbency seen at 1 μg/ml of IgG. This was correlated to the similar absorbency on the IgG curve to which no free NIP was added and referred to the actual concentration of IgG. Background in the system was defined as the signal achieved with all the reagents except the chimeric antibody. 0.2% Tween 20 was used as sole blocking agent unless otherwise stated. All experiments were performed at least three times. Data shown are representative experiments indicated as means of duplicates.

To investigate the influence of Tween 20 on TCC deposition, Tween 20 was used in concentrations from 0.4% to 0.0025%. Experiments without blocking agents were also performed. Furthermore, Tween 20 was replaced with 0.2% gelatine (Chemie Brunschwig, Basle, Switzerland) as blocking agent in all steps in some experiments.

To study the deposition of complement on another protein, 100 μL 1 μL/ml rabbit Fab fragments haptenized with NIP in a similar way as described for BSA were coated to the polystyrene wells.

Sandwich complement activation assay. An alternative complement activation assay was constructed to further investigate the TCC binding. 100 μl 0.5 μg/ml of the IgG3 chimeric antibody was adsorbed to polystyrene wells overnight at room temperature. 100 μl 10 μg/ml NIP-BSA diluted in PBS with 0.2% Tween 20 was then added and incubated for 45 min at 37° C. Subsequently an additional portion of the chimeric antibody (0.5 μg/ml) was added. Serum diluted to 1% VBS with 0.2% Tween 20 was used as complement source. The rest of the assay was performed as described for the solid phase complement activation assay. In control experiments NIP-BSA was added to uncoated plates. Additionally, the NIP-BSA step was omitted and also the second chimeric antibody portion. Moreover, the complement source was incubated in 10 mM EDTA-VBS and all experiments were also performed with 0.2% gelatine as the only blocking reagent. In order to elute the NIP-BSA complex from the antibody two different procedures were used: 1) 0.2M NIP was added either before or after the serum step. 2) Pepsin (Sigman, St. Louis, Mo, U.S.A.) in acetate buffer pH 4.0 was added after the serum step and incubated for 45 min. The substrate ratio was 1:50 (w/w). To investigate the proteolytic and pH effect on TCC bound to the plastic surface, zymosan activated serum diluted 1:10,000 was adsorbed over night to polystyrene plates. Moreover, the elution of BSA was investigated, by using polyclonal anti-human serum albumin (Dakopatts) cross-reacting with BSA instead of anti-TCC. To control for classical complement activation, binding of Clq, C4, C3 and C 5 was also investigated. All experiments were performed at least three times. Data shown are representative experiments indicated as mean of sixplicates.

Analyses of fluid phase complement activation products. Complement activation was assessed in two enzyme immuno assays specific for neoepitopes specifically expressed on activation products. One was specific for C3 activation products, thus evaluating the initial part of the complement cascade. In brief, polystyrene plates were coated with a mouse monoclonal antibody (bH6) specific for a C3 neoepitope expressed on C3b, iq3b and C3c, but not on native C3. A rabbit anti-human C3c antiserum (Behring) was used in the second antibody layer. Finally, a peroxidase conjugated anti-rabbit Ig was added (Amersham). The rest of the assay was performed as described for the solid phase complement activation assay and referred to a standard of zymosan activated serum defined to contain 1000 AU/ml. The other assay detected the fluid phase SC5b-9 terminal complement complex (TCC). In brief, polystyrene plates were coated with a mouse monoclonal antibody (aE11) specific for a neoepitope expressed in activated C9. A rabbit anti-human C5 antiserum (Dakopatts) was used in the subsequent antibody stop. The rest of the assay was performed as described for the C3 activation assay.

Results

Binding of chimeric antibody to NIP-BSA. A dose-dependent binding curve was obtained after addition of different concentrations of chimeric IgG3 anti-NIP to NIP-BSA absorbed to polystyrene (FIG. 10). By adding 0.2 mM NIP to the wells before or after addition of serum only 4% (0.04 μg/ml) and 6% (0.06μg/ml) of the antibody remained bound to the NIP-BSA aggregates, respectively. No elution of anti-NIP was obtained if NIP was added after the detection antibodies. Similar binding of the anti-NIP antibody was observed with or without the presence of normal human serum, with EDTA-serum, or with heat-inactivated serum. No non-specific binding was observed when the anti-NIP antibody was added to uncoated wells in the presence of 0.2% Tween 20.

Clq binding. Microplates coated with NIP-BSA were incubated with the anti-NIP antibody and subsequently with normal serum, serum diluted in EDTA-VBS, or heat inactivated serum (FIG. 10)). A dose-dependent binding of Clq was observed when normal serum was added. The binding was significantly diminished when 10 mM EDTA-serum was used. Clq binding was completely abolished when the anti-NIP antibody was eluted by addition of NIP before serum. When the anti-NIP antibody was eluted after the addition of serum a reduction in the binding of Clq was found comparable to that found for EDTA-serum. No clq binding was obtained when the anti-NIP antibody was coated directly to the polystyrene surface or when heat-inactivated Serum was used as C source.

C4 and C3 binding. Virtually identical dose-dependent binding patterns were observed for C4 and C3 (FIG. 11). This binding remained unchanged when elution of the antibody with soluble NIP was performed after addition of serum. When NIP was added before the C source no binding was seen as observed for C1q. No binding was observed when EDTA-serum or heat inactivated serum was used.

TCC formation. The formation of TCC on the AG-antibody complex was investigated. A similar dose-dependent curve was obtained both for the anti-C5 antibody and the anti-C9 neoepitope mAb (FIG. 12). The latter recognizes activated C9 incorporated in TCC. The results were virtually identical to those obtained for C4 and C3. To further examine whether TCC was associated with the protein or with the polystyrene surface, increasing amounts of NIP-BSA were adsorbed to the polystyrene plates (0 µg/ml, 1 µg/ml, 10 µg/ml, 100 µg/ml and 1 mg/ml. An aliquot of 1 µg/ml anti-NIP was then added before the C source. Increased deposition of TCC correlating with the NIP-BSA were (FIG. 13) TCC did not bind when the NIP-BSA coat was omitted. Furthermore, if the antibody was adsorbed directly to the plastic overnight, no binding of TCC was seen.

We then tested for deposition of S-protein in association with TCC. The S-protein was found to bind very well directly to the plastic surface. With increasing amounts of anti-NIP/NIP-BSA on the plates a decreased binding of the S-protein was found (FIG. 13). The S-protein bound equally well in normal serum and in EDTA-serum, indicating that the binding was independent of C activation.

Control experiments were performed to exclude a possible binding of TCC to Tween 20. When Tween 20 was replaced by 0.2% gelatin as blocking reagent in all steps, the specific TCC signal was fully maintained and no unspecific binding was observed. We did not observe any diminished binding of TCC by reducing the concentration of Tween 20 sequentially in all buffer steps. On the contrary, a slight increase in the binding of TCC was observed when the Tween 20 concentration was reduced below 0.05% and by excluding Tween 20 completely from the buffers an increased nonspecific binding of TCC was observed in the well with no chimeric antibody added.

The binding patterns for C1q,C4 and TCC were similar for NIP rabbit Fab fragments as described for BIP-BSA above.

C binding to immune complexes in the sandwich assay. C1q, C4, C3 and TCC bound in the alternative sandwich C activation assay consisting of a first layer of anti-NIP antibody, a second layer of NIP-BSA and a third layer of anti-NIP antibody. However, by subsequently excluding each of these layers this binding was completely abolished. Similar results were observed with Tween 20 and gelatine as blocking reagents.

In this model we are not able to elute NIP-BSA by adding free NIP after serum. However, if NIP was added before serum no C binding or BSA was observed. Binding of TCC to the immune complexes was further studied in addition of pepsin (FIG. 14). TCC and BSA were removed when pepsin was added, but remained bound in the buffer control. In similar experiments with zymosan activated serum passively adsorbed to polystyrene plates the expression of the C9 neoepitope was unchanged after addition of pepsin.

Fluid phase C3 activation and. TCC formation. To investigate whether the C activation by the immune complexes was reflected in the fluid phase, we tested the supernatants from the solid phase C activation assay. A dose-dependent curve was obtained of fluid phase C3 activation (FIG. 15) which was almost parallel to the C3 deposition on the solid phase. The EDTA-serum control was negative. The TCC deposition on the solid phases was not reflected by a dose response increase of TCC in the fluid phases.

References

1. Michaelsen, T. E., et al. *Biol. Chem.* 1977. 252:883.
2. Huck, S., et al. *Nucleic Acids Res.* 1986. 14:1779.
3. Bindon, C. I., et al. *J. Exp. Med.* 1988. 168:127.
4. Krawinkel, U. and Rabbitts, T. H., *EMBO J.* 1982. 1:403.
5. Beale, D. and Feinstein, A., *Quarterly Reviews of Biophysics.* 1976. 9:135.
6. Oi, V. T., *Nature.* 1984. 307:136.
7. Gregory, L., et al. *Mol. Immunol.* 1987. 24:221.
8. Schumaker, V. N., et al. *Biochemistry.* 1976. 15:5175.
9. Brüggemann, M., et al. *J. Exp. Med.* 1987. 166:1351.
10. Neuberger, M. S., et. al. *Nature.* 1985. 314:261.
11. Schneider, W. P., et al. *Proc. Natl. Acad. Sci. U.S.A.* 1988. 85:2509.
12. Burton, D. R., *Molecular Immunol.* 1985. 22:123
13. Boulianne, G. L. et al. *Nature.* 1984. 312:643
14. Morrison, S. L., et al. *Proc. Natl. Acad. Sci. U.S.A.* 1984. 81:6851.
15. Neuberger, M. S., et al. *Nature.* 1984. 312:604.
16. Jones, P. T., et al, *Nature.* 1986. 321:522.
17. Neuberger, M. S., *EMBO J.* 1983. 2:1373.
18. Maniatis, T., et al. *Molecular cloning,* Cold Spring Harbor Laboratory, Cold Spring Harbor, NY. 1982.
19. Oi, V. T., et al. *Proc. Natl. Agad. Sci. U.S.A.* 1983. 80:825.
20. Potter, H., et al. *Proc. Natl. Acad. Sci. U.S.A.* 1984. 81:7161.
21. Avrameas, S., Immunochemistry. 1969. 6:43.
22. Mulligan, R. C. and Berg, P., *Proc. Natl. Acad. Sci. U.S.A.* 1981. 78:2072.

We claim:
1. A modified IgG3 antibody containing a human IgG3 constant region, wherein a hinge region of said modified IgG3 antibody contains a deletion of the 17 amino acid sequence of exon 1.
2. Modified IgG3 as claimed in claim 1, being a truncated variant in which the number of repeats of the 15 amino acid sequence in the hinge region has been reduced whereby a shortened hinge region is provided.
3. Modified IgG3 as claimed in claim 2, wherein the hinge region comprises a single repeat of the native 15 amino acid sequence.
4. Modified IgG3 as claimed in claim 1, which is a chimeric IgG3 comprising variable antigen binding domains from a non-human species and human constant regions.
5. Modified IgG3 as claimed in claim 4, comprising mouse variable regions and human constant regions.
6. A recombinant DNA molecule encoding modified IgG3 as claimed in claim 1.
7. An expression vector permitting expression within a mammalian cell line, comprising a recombinant DNA molecule as claimed in claim 6 operatively linked to an expression control sequence.
8. A mammalian cell line transfected with a recombinant DNA molecule as claimed in claim 6.
9. Modified IgG3 antibodies containing human IgG3 constant regions which have a shorter total-hinge region compared with normal human IgG3, comprising a hinge region sequence selected from the group consisting of:
Glu Pro Lys Ser Cys Asp Thr Pro Pro Pro Cys Pro Ser Cys Pro (SEQ ID NO:2);
Glu Pro Lys Ser Cys Asp Cys Pro Ser Cys Pro (SEQ ID NO:3); and
Glu Ser Lys Tyr Cys Asp Cys Pro Ser Cys Pro (SEQ ID NO:4).
10. Modified IgG3 as claimed in claim 9, which is a chimeric IgG3 comprising variable antigen binding domains from a non-human species and human constant regions.
11. Modified IgG3 as claimed in claim 10, comprising mouse variable regions and human constant regions.
12. A recombinant DNA molecule encoding modified IgG3 as claimed in claim 9.
13. An expression vector permitting expression within a mammalian cell line, comprising a recombinant DNA molecule as claimed in claim 12 operatively linked to an expression control sequence.
14. A mammalian cell line transfected with a recombinant DNA molecule as claimed in claim 12.

* * * * *